(12) United States Patent
Braun

(10) Patent No.: US 11,648,000 B2
(45) Date of Patent: May 16, 2023

(54) VERTEBRAL PROBES AND RELATED SURGICAL METHODS

(71) Applicant: Cricket K. Braun and John T. Braun, MD Family LLC, Charlotte, VT (US)

(72) Inventor: John T. Braun, Charlotte, VT (US)

(73) Assignee: Braunvest LLC, Charlotte, VT (US)

( * ) Notice: Subject to any disclaimer, the term of this patent is extended or adjusted under 35 U.S.C. 154(b) by 393 days.

(21) Appl. No.: 16/526,664

(22) Filed: Jul. 30, 2019

(65) Prior Publication Data

US 2020/0029949 A1    Jan. 30, 2020

Related U.S. Application Data

(60) Provisional application No. 62/712,158, filed on Jul. 30, 2018.

(51) Int. Cl.
| | |
|---|---|
| *A61B 17/16* | (2006.01) |
| *A61B 17/02* | (2006.01) |
| *A61B 17/17* | (2006.01) |
| *A61F 2/46* | (2006.01) |
| *A61B 17/00* | (2006.01) |
| *A61B 34/20* | (2016.01) |

(52) U.S. Cl.
CPC ...... *A61B 17/025* (2013.01); *A61B 17/00234* (2013.01); *A61B 17/1671* (2013.01); *A61B 17/1757* (2013.01); *A61F 2/46* (2013.01); *A61B 34/20* (2016.02); *A61B 2017/00238* (2013.01); *A61B 2017/0256* (2013.01)

(58) Field of Classification Search
CPC ................ A61B 17/1604; A61B 17/1655
See application file for complete search history.

(56) References Cited

U.S. PATENT DOCUMENTS

| | | | | |
|---|---|---|---|---|
| 5,318,570 | A | * 6/1994 | Hood | A61B 17/8847 601/2 |
| 5,387,213 | A | 2/1995 | Breard et al. | |
| 5,827,290 | A | * 10/1998 | Bradley | A61B 17/1604 606/85 |
| 5,951,560 | A | 9/1999 | Simon et al. | |
| 6,299,613 | B1 | 10/2001 | Ogilvie et al. | |
| 7,285,121 | B2 | 10/2007 | Braun et al. | |
| 7,297,146 | B2 | 11/2007 | Braun et al. | |
| 7,637,978 | B2 | 12/2009 | Jung | |
| 7,691,131 | B2 | 4/2010 | Graf | |
| 7,727,258 | B2 | 6/2010 | Graf | |

(Continued)

FOREIGN PATENT DOCUMENTS

| | | |
|---|---|---|
| WO | WO2009128074 | 10/2009 |
| WO | WO2017127532 | 7/2017 |

*Primary Examiner* — Zade Coley
(74) *Attorney, Agent, or Firm* — Matthew D. Thayne; Thayne and Davis LLC

(57) ABSTRACT

Vertebral probes for fusionless spinal surgeries and related surgical methods. In some embodiments, the probe may comprise a shaft having one or more tapering portions. Some embodiments may further comprise one or more non-tapering portions. The probe may further comprise a distal tip extending from a shelf or ledge that may allow for penetration of the tip therethrough with a first force and be configured to inhibit further advancement of the probe by requiring a second force substantially greater than the first force to achieve further advancement.

20 Claims, 6 Drawing Sheets

(56) References Cited

U.S. PATENT DOCUMENTS

| | | |
|---|---|---|
| 7,845,945 B2 | 12/2010 | Canter |
| 8,172,880 B2 | 5/2012 | Graf |
| 8,177,810 B2 | 5/2012 | Ferree |
| 8,221,457 B2 | 7/2012 | Delecrin et al. |
| 8,641,736 B2 | 2/2014 | Marik et al. |
| 8,979,874 B2 | 3/2015 | Darois et al. |
| 9,433,442 B2 | 9/2016 | Lindemann et al. |
| 9,833,230 B2 | 12/2017 | Stone |
| 10,179,015 B2 | 1/2019 | Lavigne et al. |
| 2002/0032447 A1* | 3/2002 | Weikel ............... A61B 17/7061 606/86 R |
| 2002/0055783 A1* | 5/2002 | Tallarida ............ A61B 17/1764 623/20.14 |
| 2002/0077641 A1* | 6/2002 | Michelson ......... A61B 17/1757 606/167 |
| 2002/0082598 A1 | 6/2002 | Teitelbaum |
| 2002/0143343 A1* | 10/2002 | Castro ............... A61B 17/1757 606/90 |
| 2002/0173794 A1* | 11/2002 | Happonen .......... A61B 17/1655 606/79 |
| 2003/0018337 A1* | 1/2003 | Davis ................. A61B 17/1655 606/80 |
| 2003/0036764 A1* | 2/2003 | Hamada .............. A61L 27/365 606/102 |
| 2003/0109883 A1* | 6/2003 | Matsuzaki .......... A61B 17/1604 606/86 R |
| 2005/0070907 A1* | 3/2005 | Abernathie ........ A61B 17/1655 606/80 |
| 2005/0171551 A1* | 8/2005 | Sukovich ........... A61B 17/7082 606/86 R |
| 2006/0235306 A1* | 10/2006 | Cotter ............... A61B 17/1688 600/459 |
| 2007/0219554 A1* | 9/2007 | Landry .............. A61B 17/1703 623/17.16 |
| 2009/0312782 A1* | 12/2009 | Park .................. A61B 17/3468 606/184 |
| 2010/0131010 A1 | 5/2010 | Graf |
| 2011/0054537 A1* | 3/2011 | Miller ............... A61B 17/7044 606/279 |
| 2011/0238069 A1* | 9/2011 | Zajac ................ A61B 17/1655 606/79 |
| 2012/0189984 A1 | 7/2012 | Holmes |
| 2013/0253587 A1 | 9/2013 | Carls et al. |
| 2016/0374661 A1* | 12/2016 | Housman .......... A61B 17/861 606/232 |
| 2020/0155728 A1* | 5/2020 | Brunelle ............ A61B 17/1615 |

* cited by examiner

VERTEBRAL PROBES AND RELATED SURGICAL METHODS

CROSS-REFERENCE TO RELATED APPLICATIONS

This application claims the benefit under 35 U.S.C. § 119(e) of U.S. Provisional Patent Application No. 62/712,158, which was filed Jul. 30, 2019 and titled "VERTEBRAL PROBES AND RELATED SURGICAL METHODS," which is hereby incorporated herein by reference in its entirety.

SUMMARY

Embodiments of apparatus and methods are disclosed herein that relate to bone probes. In some specific embodiments disclosed herein, such probes may comprise vertebral probes that may be used in certain spinal surgeries, particularly fusionless spinal surgeries, such as scoliosis surgeries.

Surgeons often use pedicle probes as vertebral probes to prepare for placement of bone screws in a patient's vertebral column. However, such probes are not designed for use in vertebral bodies and suffer from several drawbacks that make them less than ideal for this use. For example, such probes typically lack any features that allow a surgeon to feel or otherwise readily determine the placement of the probe within the vertebral body, that inhibit the probe from being advanced too far through a vertebral body, and/or that allow a surgeon to very precisely select an appropriate screw length for subsequent fixation to the vertebrae.

The present inventor has therefore determined that it would be desirable to provide systems and methods that overcome one or more of the foregoing limitations and/or other limitations of the prior art. Thus, in a more specific example of a vertebral probe, the probe may comprise a shaft having one or more tapering portions. Some embodiments may further comprise one or more non-tapering portions. The probe may comprise a distal tip extending from a shelf or ledge that may allow for penetration of the tip therethrough with a first force and be configured to inhibit further advancement of the probe by requiring a second force substantially greater than the first force to achieve further advancement.

In some embodiments, the probe may comprise one or more sections having a circular cross-section and the tip may comprise a non-circular cross-section, in whole or in part, such as flattened upper and/or lower surfaces forming a "duckbill" shape extending from a distal end of the probe.

Some embodiments may further comprise various other features, such as sections having distinct markings to indicate generally a current position of the probe within a vertebral body. Such markings may vary section by section to provide an easy way of visualizing advancement of the probe at one or more critical steps during a probing procedure. More precise markings may be provided to allow a surgeon to select a specific bone screw or other anchor for subsequent fixation to the vertebrae.

In a specific example of a vertebral probe for use in spinal surgeries, the probe may comprise a shaft having a circular cross section at least in part and a tip positioned at a distal end of the shaft and configured to penetrate a vertebral body to facilitate subsequent placement of a bone anchor providing bicortical purchase within the vertebral body. The tip may comprise a non-circular shape in cross-section at least in part.

In some embodiments, the shaft may comprise a tapering portion and a non-tapering portion. In some such embodiments, the non-tapering portion may be positioned adjacent to the tip. In some embodiments, the shaft may further comprise a second non-tapering portion, wherein the tapering portion is positioned in between the non-tapering portion and the second non-tapering portion.

In some embodiments, the tip may be defined, at least in part, by opposing flat surfaces extending from the shaft. The shaft may further comprise one or more shelves that may extend at an angle (in some embodiments a perpendicular or at least substantially perpendicular angle) relative to at least one of the opposing flat surfaces of the tip. In some such embodiments, the shaft may comprise two opposing shelves extending an angle relative to each of the two opposing flat surfaces of the tip.

In some embodiments, the vertebral probe may be configured to allow for penetration of the tip through a cortical wall of a vertebral body with a first force and further configured to inhibit further advancement of the vertebral probe by requiring a second force substantially greater than the first force to achieve further advancement of the vertebral probe within the vertebral body.

In some embodiments, the shaft may comprise a plurality of markings configured to allow a user to identify a current position of the vertebral probe within a vertebral body. In some such embodiments, the plurality of markings may comprise a plurality of marking sections, wherein each marking section is visually distinguishable from an adjacent marking section other than with distinct alphanumeric characters such that the plurality of marking sections is configured to provide a user with an indication of an extent to which the vertebral probe has penetrated a vertebral body without use of alphanumeric characters.

In another example of a vertebral probe according to some embodiments, the probe may comprise a shaft comprising at least one tapering portion and at least one non-tapering portion and a tip positioned at a distal end of the shaft and configured to penetrate a vertebral body to facilitate subsequent placement of a bone anchor providing bicortical purchase within the vertebral body. The tip may be set apart from the shaft at a shelf defining an engaging surface for increasing an insertion force of the vertebral probe during advancement through a vertebral body. The tip may be lacking in any sharp points.

In some embodiments, the tip may comprise a non-circular shape in cross section.

In some embodiments, the shelf may extend about an entire periphery of the tip.

Some embodiments may further comprise a second shelf defining a second engaging surface for increasing an insertion force of the vertebral probe during advancement through a vertebral body.

In some embodiments, the tip may be defined, at least in part, by opposing flat surfaces extending from the shaft. In some such embodiments, the tip may be further defined by opposing tapered edges extending to a rounded and blunt tip.

In an example of a method for preparing a vertebral body for receipt of a bicortical bone anchor according to some implementations, the method may comprise advancing a tip of a vertebral probe through a proximal cortical wall of a vertebral body. The vertebral probe may comprise a shelf defining a boundary between a shaft of the vertebral probe and the tip. The method may further comprise engaging the shelf with an outer surface of the proximal cortical wall to inhibit further advancement of the tip.

Some implementations may further comprise rotating the vertebral probe to form a chamber, such as a chamber having a circular cross section, within the vertebral body adjacent to the proximal cortical wall.

Some implementations may further comprise, following the step of rotating the vertebral probe, advancing the vertebral probe through the vertebral body such that the tip contacts and penetrates the distal cortical wall of the vertebral body and engaging the shelf with an inner surface of the distal cortical wall to inhibit further advancement of the tip.

In some implementations, following the step of engaging the shelf with an inner surface of the distal cortical wall, the vertebral probe may be rotated again to form a circular opening at the distal cortical wall.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
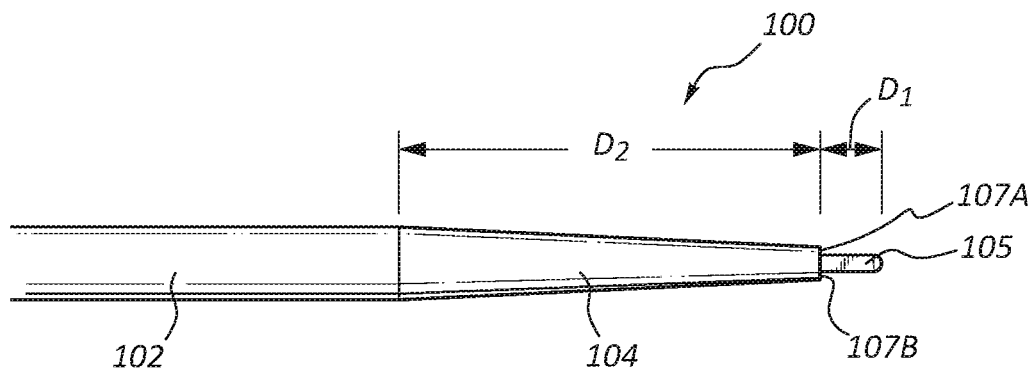
FIG. 1 is a side elevation view of a vertebral probe according to some embodiments.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

As used herein, the term "substantially" refers to the complete or nearly complete extent or degree of an action, characteristic, property, state, structure, item, or result to function as indicated. For example, an object that is "substantially" cylindrical or "substantially" perpendicular would mean that the object/feature is either cylindrical/perpendicular or nearly cylindrical/perpendicular so as to result in the same or nearly the same function. The exact allowable degree of deviation provided by this term may depend on the specific context. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

Similarly, as used herein, the term "about" is used to provide flexibility to a numerical range endpoint by providing that a given value may be "a little above" or "a little below" the endpoint while still accomplishing the function associated with the range.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

FIG. 1 depicts a vertebral probe 100 that may be used for various surgical procedures, such as, in preferred embodiments and implementations, scoliosis or other fusionless spinal surgeries. To provide a more particular example, probe 100 may be used to facilitate screw or other anchor placement in a vertebral body or other bone. The depicted vertebral probe 100 is specifically configured to facilitate bicortical purchase prior to placement of a vertebral screw (not shown) that extends all the way through the vertebral body—i.e., through the proximal cortical wall, through the cancellous bone, and through the distal cortical wall. Placement of screws or other anchors in this manner may be particularly useful for fusionless scoliosis surgical procedures, which typically require high strength attachment points to the spinal column and therefore often warrant use of screws that extend through two opposing cortical walls of a vertebral body. Because such procedures are typically performed in very sensitive areas of patient anatomy and can be very dangerous, it may be useful to provide a probe to make the screw placement procedure safer and/or easier.

Probe 100 provides various features that may be useful for these and/or other purposes. For example, probe 100 comprises a cylindrical portion 102, a tapering portion 104, and a tip 105. Tip 105 is designed to facilitate precise, safe, and/or repeatable positioning of probe 100 through a vertebral body, which may be useful to guide bone screws or other anchors through the vertebral body, particularly when bicortical purchase of the screws/anchors is required or desired.

Thus, tip 105 comprises a shape that, in at least one dimension, is less than that of the adjacent probe body (in the depicted embodiment tapering portion 104) so as to create one or more ledges or shelves 107, the purpose of which will be explained below. In the depicted embodiment, two shelves 107A and 107B are formed above and below tip 105, as shown in FIG. 1. Although for some uses it may be preferred to provide one or more sharp and/or distinct shelves, as shown in FIG. 1 (tip 105 extends at least substantially at a right angle relative to shelves 107A and 107B), it is contemplated that in other embodiments one or more tapering, smooth, and/or otherwise less sharp shelves may be formed instead. As also shown in FIG. 1, tip 105 may comprise flattened upper and/or lower surfaces so as to form a plate or plate-like shape. Thus, in some preferred embodiments, tip 105 may differ, sharply differ in some such embodiments, from the shape of the shaft of probe 100 adjacent to tip 105, which may be rounded or at least substantially rounded in cross-section.

Other tip shapes are contemplated, however. For example, in alternative embodiments, tip 105 may comprise bulbous, curved, and/or rounded surfaces. Similarly, although smooth surfaces may be preferred for certain applications and embodiments, it is also contemplated that roughened surfaces may be useful for certain procedures. Similarly, although the distal end of tip 105 is rounded, as shown in both FIGS. 1 and 2, when viewed from both the side view of FIG. 1 and the top view of FIG. 2, in other embodiments it may be desirable to form tip 105 with a sharpened distal end, which sharpening may take place in one or more dimensions so as to form, for example, either a sharpened blade-like tip or a pointed tip at the distal end of probe 100. However, for many applications it may be preferred to configure the distal end of the tip 105 specifically to avoid or be devoid of any sharp points or edges, given, for example, the nature of the delicate anatomy surrounding the vertebral column. Thus, in preferred embodiments and implementations the tip may be rounded or otherwise blunt and/or non-sharp. However, it may be provided to provide a blunt tip that is not smooth. In other words, the distal surface of the tip 105 that is configured to contact a cortical wall of a vertebral body may be surface roughened to prevent slippage.

Again, providing a blunt tip that avoids sharp points and/or edges may be desirable around sensitive patient anatomy and may be feasible due to the cortical wall of the vertebral bodies being less hard and easier to penetrate than other areas of the spine, such as the pedicle region of the spine. For similar reasons, it may be preferred to form the tip 105 and/or the entire probe as unthreaded. Thus, unlike a tap or other known devices, which may be difficult to back out and re-advance in the proper direction, providing a dull/blunt, unthreaded tip may allow for precise positioning through the cortical wall of a vertebral body and may allow for precise advancement without destroying the ability of a subsequent bone screw or other bone anchor to obtain proper purchase within the vertebral body.

One or more features of probe 100 proximal of tip 105 may also be provided to improve functionality for certain procedures, such as to prepare a vertebral body for acceptance of a bicortical-purchase screw or other bone anchor for use in, for example, fusionless scoliosis surgeries and the like. For example, the embodiment depicted in FIGS. 1 and 2 comprises a non-tapering and/or cylindrical section 102 and a tapering section 104 positioned adjacent to and distal of non-tapering section 102. As described in greater detail below, providing a tapering section 104 increases the force required in order to tamp the probe through a vertebral body or other bone portion. This may be useful to prevent the probe from being tamped too far across the vertebral body and thereby allow for greater control during the process of inserting the probe and particularly at or around the critical time of breach of the distal cortical wall, since the tapering section increases the force required for continued advancement of the probe. As also discussed further below, other embodiments are contemplated in which one or more additional non-tapering portions, preferably of specific length and positioning on the probe, are provided in order to further facilitate ease of use and/or safety.

Figure 2:
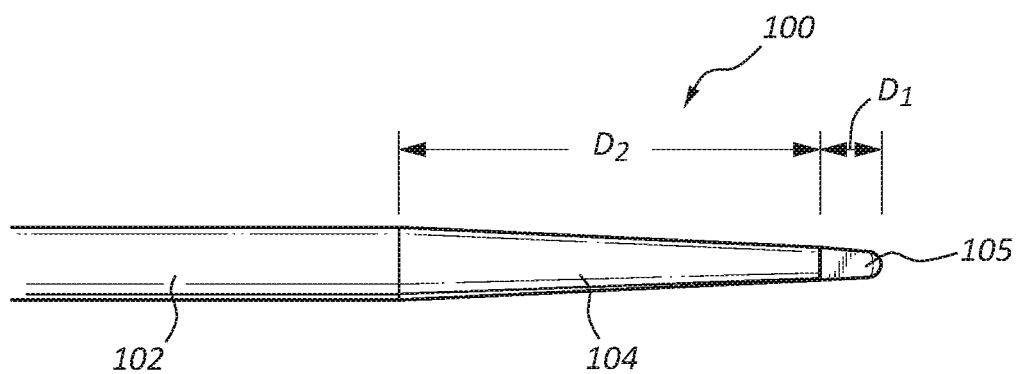
FIG. 2 is a top plan view of the vertebral probe of FIG. 1.

As shown in FIG. 2, in some embodiments, the degree of tapering on tapering section 104 may extend smoothly and apply to tip 105 when viewed from one perspective and/or in two dimensions. However, it is also contemplated that, in other embodiments, tip 105 may not be tapered in any direction/dimension or, alternatively, may taper but not smoothly with respect to tapering section 104. In other words, a ledge or shelf may be formed between tip 105 and an adjacent section, whether tapering or not, when viewed from any perspective. In other words, in some such embodiments, the shelf/ledge may extend about the entire perimeter of tip 105, or may extend about the perimeter of tip 105 along all but one side of tip 105, if desired.

The dimensions of various portions of probe 100 may also be important and may be related to particular dimensions of patient anatomy, such as the dimensions of a vertebral body and/or a specific portion/aspect of a vertebral body. For example, again with reference to FIGS. 1 and 2, there may be some preferences in terms of dimensions D1 and D2 that may impact functionality. In preferred embodiments, distance D1 may be at least as long as the distance between opposing outer cortical walls of a particular vertebral body through which the probe is to be inserted. In some such embodiments, distance D1 may be the same, or at least substantially the same, as this distance. Thus, distance D1 may vary depending upon the particular patient and/or the particular vertebral body that is to the subject of a surgical procedure.

Thus, it is contemplated that some embodiments may comprise a set of probes having different dimensions according to a particular portion of the vertebral column, such as a thoracic probe (22-35 mm) and a lumbar probe (35-45 mm). In some particularly preferred embodiments that may be generally useful for a variety of different patient anatomies, however, D2 may be between about 22 and about 35 mm for a thoracic probe and may be between about 35 and about 45 mm for a lumbar probe. Thus, more generally speaking, in certain preferred embodiments, distance D2 may be between about 20 and about 50 mm. In some such embodiments, distance D2 may be between about 22 and about 45 mm.

Similarly, although there are preferred ranges for distance D2, this distance may also vary depending upon the patient and portion of the vertebral column being probed. However, in some particularly preferred embodiments that may be generally useful for a variety of different patient anatomies, D2 may be between about 2 and about 3 mm for a thoracic probe and may be between about 3 and about 5 mm for a lumbar probe. Thus, more generally speaking, in certain preferred embodiments, distance D1 may be between about 2 and about 6 mm. In some such embodiments, distance D1 may be between about 3 and about 5 mm.

Other dimensions of probe 100 may be significant as well. For example, as previously mentioned, at least one dimension of tip 105 is preferably less than that of the adjacent portion/section of probe 100 so as to provide one or more shelves, ledges, or other features—such as shelves 107A and 107B—for providing tactile sensation indicative of probe location, as described below, and/or controlling advancement of probe 100. In addition, preferably tip 105 and/or the remaining portion of probe 100 that is configured and/or designed to extend through bone comprises a maximal cross-sectional dimension that is less than the major diameter of a thread depth of a bone screw of which probe 100 is being used to facilitate entry. It may also be preferred that, in certain embodiments, tip 105 comprises a maximal cross-sectional dimension that is less than a major diameter and/or maximal cross-sectional dimension of a tip of such bone screw.

Further, although the distal end of tip 105 is depicted as rounded, it is contemplated that, in alternative designs, providing a flattened distal end, or an at least substantially flattened distal end, may be advantageous for certain purposes.

Figure 3A:
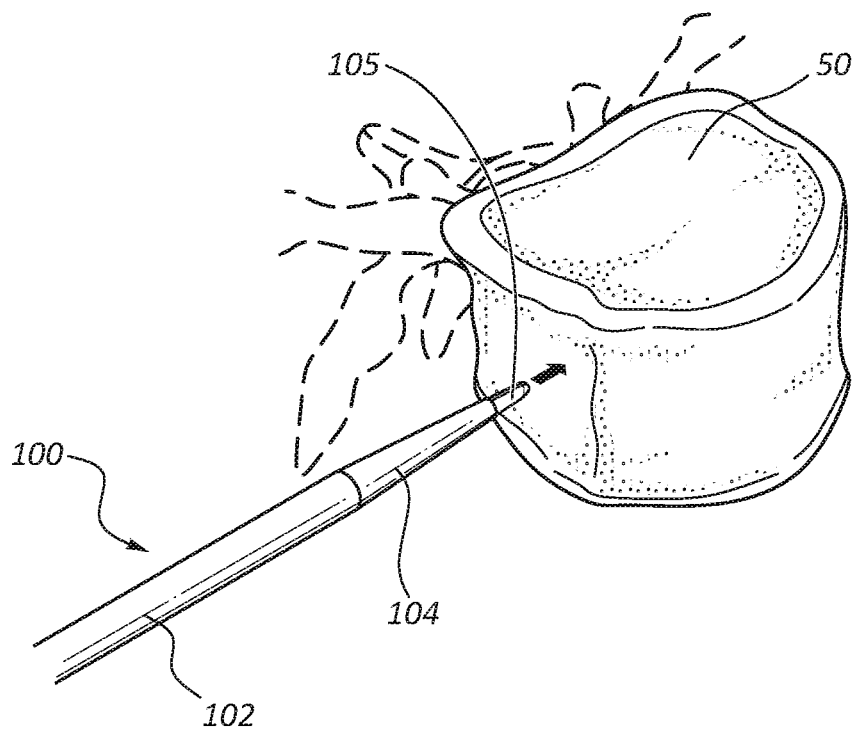
FIG. 3A is a perspective view of the vertebral probe of FIGS. 1 and 2 being advanced against the proximal vertebral cortex.

FIGS. 3A-3D depict various steps/stages during a process for using probe 100 according to certain preferred implementations of inventive methods. In FIG. 3A, tip 105 of probe 100 is advanced to contact a proximal cortical wall of a vertebral body 50. Because tip 105 is smaller than the rest of probe 100, a smaller, less invasive opening 55 (see FIG. 3B) may be formed by tamping or otherwise advancing tip 105 only through the proximal cortical wall of vertebral body 50.

Figure 3B:
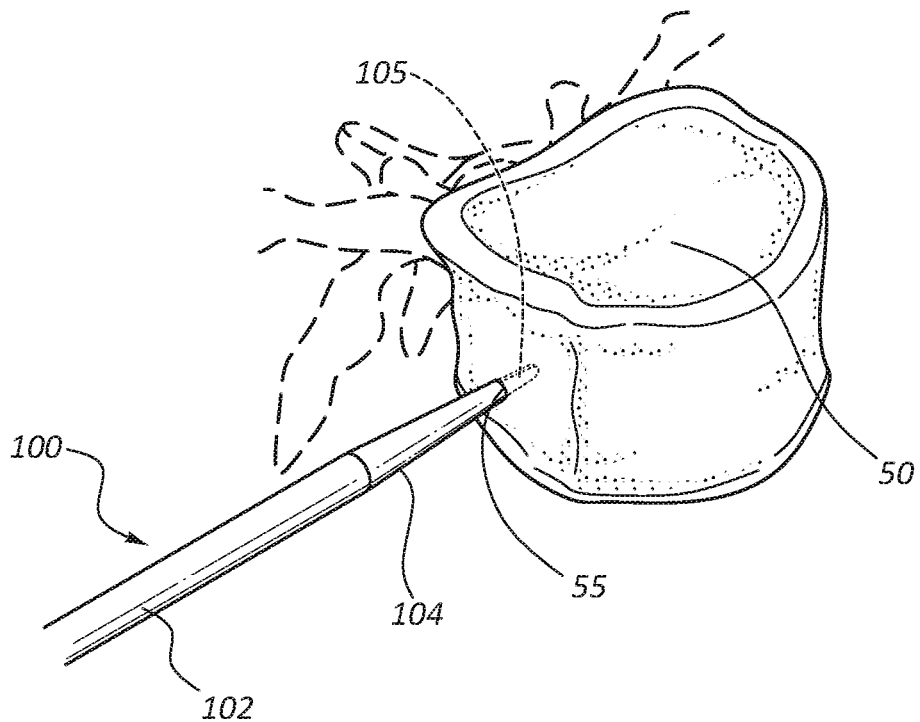
FIG. 3B is a perspective view of the vertebral probe of FIGS. 1 and 2 following penetration of a tip of the vertebral probe through the proximal vertebral cortex.

FIG. 3B depicts probe 100 following the formation of an opening in the proximal cortical wall of vertebral body 50 by tip 105. Due to the presence of one or more shelves 107, after tip 105 penetrates the cortical wall, a relatively large differential in force is required to advance probe 100 further due to the blunt shelf 107 contacting the dense cortical bone. Moreover, a surgeon may be able to, by tactile feel alone, confirm that the probe 100 is in the position depicted in FIG. 3B with the tip 105 extending into the vertebral body and the shelf 107 inhibiting further penetration.

Figure 3C:
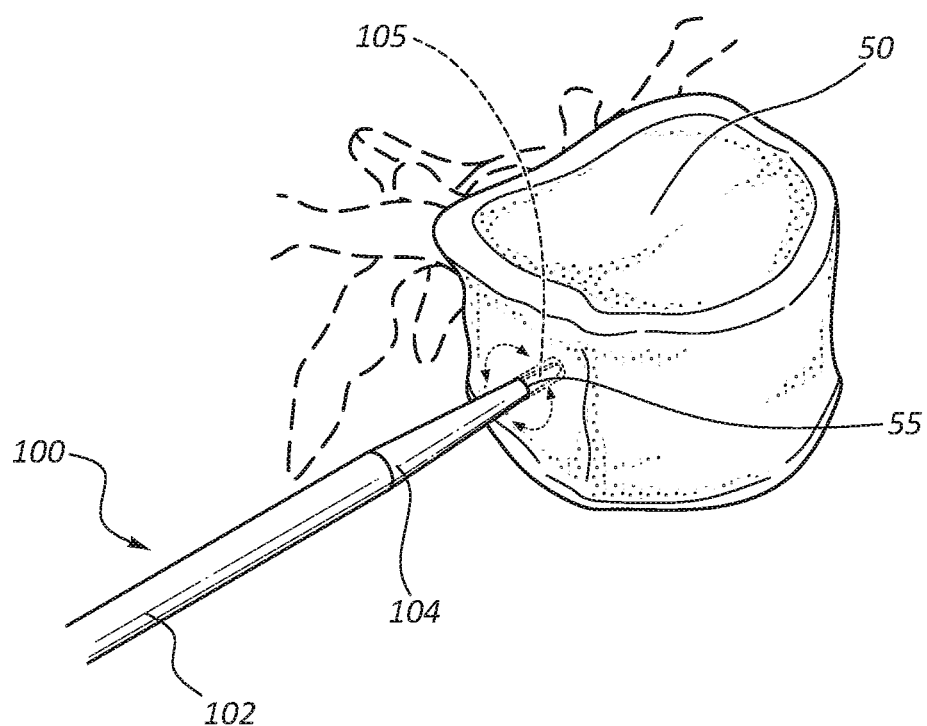
FIG. 3C is a perspective view of the vertebral probe of FIGS. 1 and 2 during the process of rotating the probe to create a chamber for further receipt of the probe therein.
Figure 6:
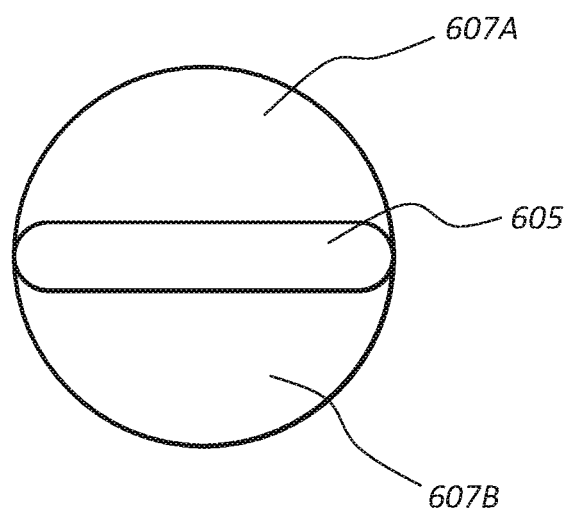
FIG. 6 is a side elevation view of a tip of a vertebral probe viewed along an elongated axis of the probe according to some embodiments.

FIG. 3C depicts the probe 100 being rotated to form a chamber with tip 105 that is circular, or at least substantially circular. This step may be performed once it has been determined that the initial penetration of the vertebral wall is in a suitable position to guide a bone screw or other anchor therethrough. Rotating the tip 105 in this manner may facilitate further penetration of probe 100 into the vertebral body 50 by providing less resistance to further tamping and/or advancement of probe 100. In some embodiments and implementations, the chamber formed by tip 105 may have the same, or at least substantially the same, diameter as the portion of the shaft immediately adjacent to tip 105. Thus, in such embodiments and implementations, the tip 105 may have a width that extends all of the way, or at least substantially all of the way, along the diameter of the adjacent shaft, as shown in FIG. 6.

Figure 3D:
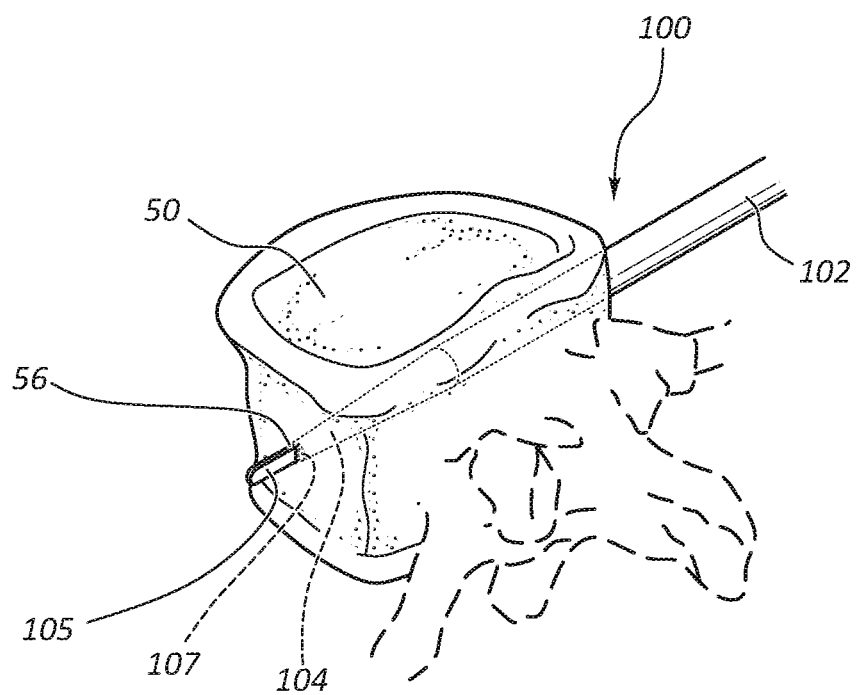
FIG. 3D is a perspective view of the vertebral probe of FIGS. 1 and 2 following penetration of the tip of the vertebral probe through the distal vertebral cortex.

FIG. 3D depicts probe 100 after it has been fully extended through opposing cortical walls of vertebral body 50. Thus, in addition to proximal opening 55, a distal opening 56 through the distal cortical wall is formed by tip 105. As previously mentioned, tapering portion 104 preferably extends through the entire, or at least substantially the entire, length of at least the cancellous bone of vertebral body 50, so as to provide continued resistance during tamping/advancement of probe 100 and prevent the probe from extending too far into and/or through vertebral body 50.

As also illustrated in FIG. 3D, shelf 107 is in contact with the inner cortical wall of vertebral body 50. Again, as discussed in connection with the penetration of probe 100 through the proximal cortical wall, shelf 107 may prevent or at least inhibit further advancement of probe 100 after tip 105 has extended through the distal cortical wall and/or may provide a surgeon with a tactile sensation to indicate the position of probe 100 illustrated in FIG. 3D. Thus, by providing a length of tip 105 that takes into account the available space adjacent to a particular vertebral body, the probing procedure and/or the following bone screw placement procedure may be made safer and more precise.

Although not shown in the figures, it is also contemplated that probe 105 may be rotated again following penetration through the distal cortical wall, similar to the rotation discussed above in connection with FIG. 3C. This may provide for a rounded hole that may be more suitable for guidance of the tip of a bone screw or anchor for bicortical screw purchase.

Figure 4:
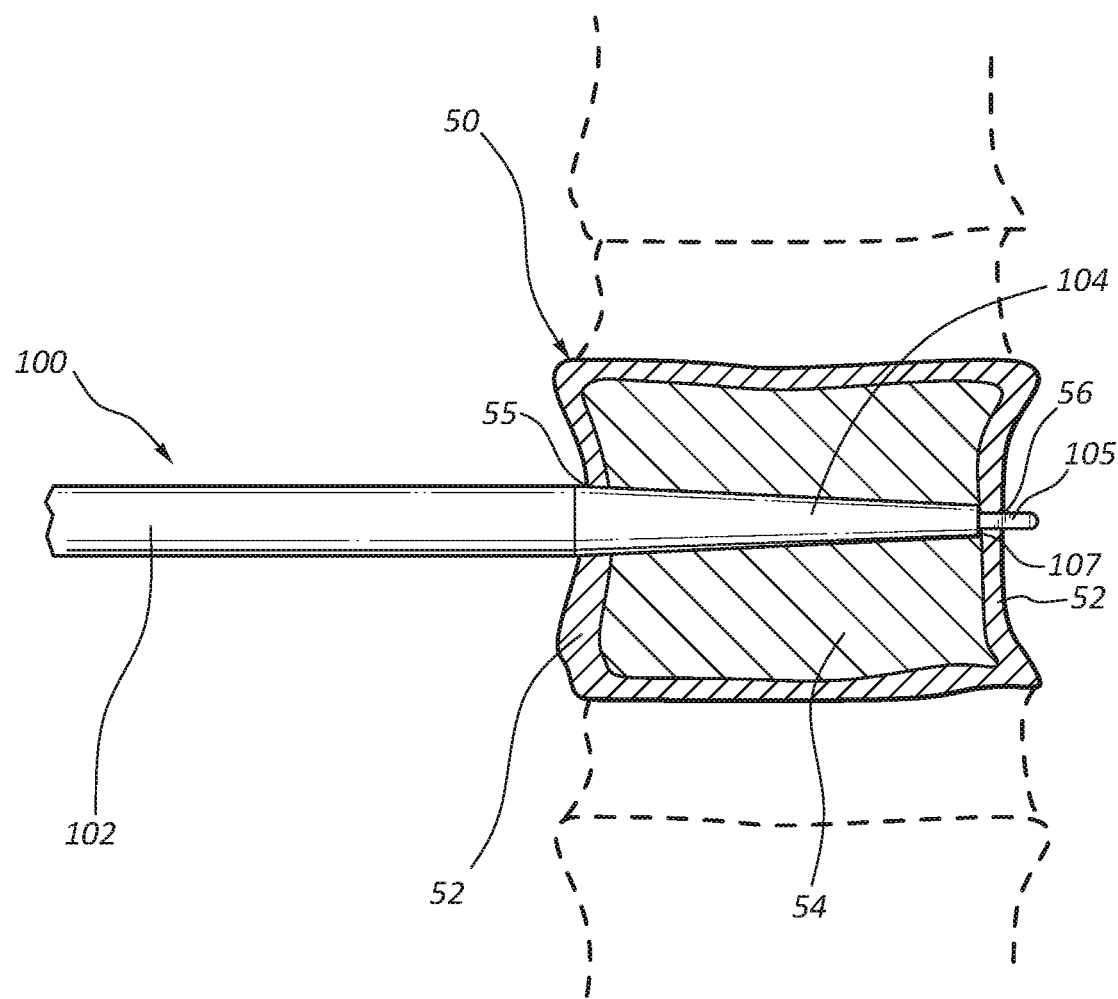
FIG. 4 is a cross-sectional view of a vertebral probe according to some embodiments fully extending through a vertebral body with the probe tip extending through the distal vertebral cortex of the body.

FIG. 4 is a cross-sectional view of probe 100 fully extended through vertebral body 50 with shelf 107 contacting the inner cortical wall 52 and tapering portion 104 extending through the cancellous core 54 of vertebrae 50. As shown in this figure, tapering portion 104 is configured to at least substantially match the width of vertebrae 50 in that it terminates just outside the proximal opening 55 in cortical shell 52. However, other embodiments are contemplated that may include non-tapering portions configured to extend into a vertebral body, as discussed below, or that taper along the entire length of the probe.

Figure 5:
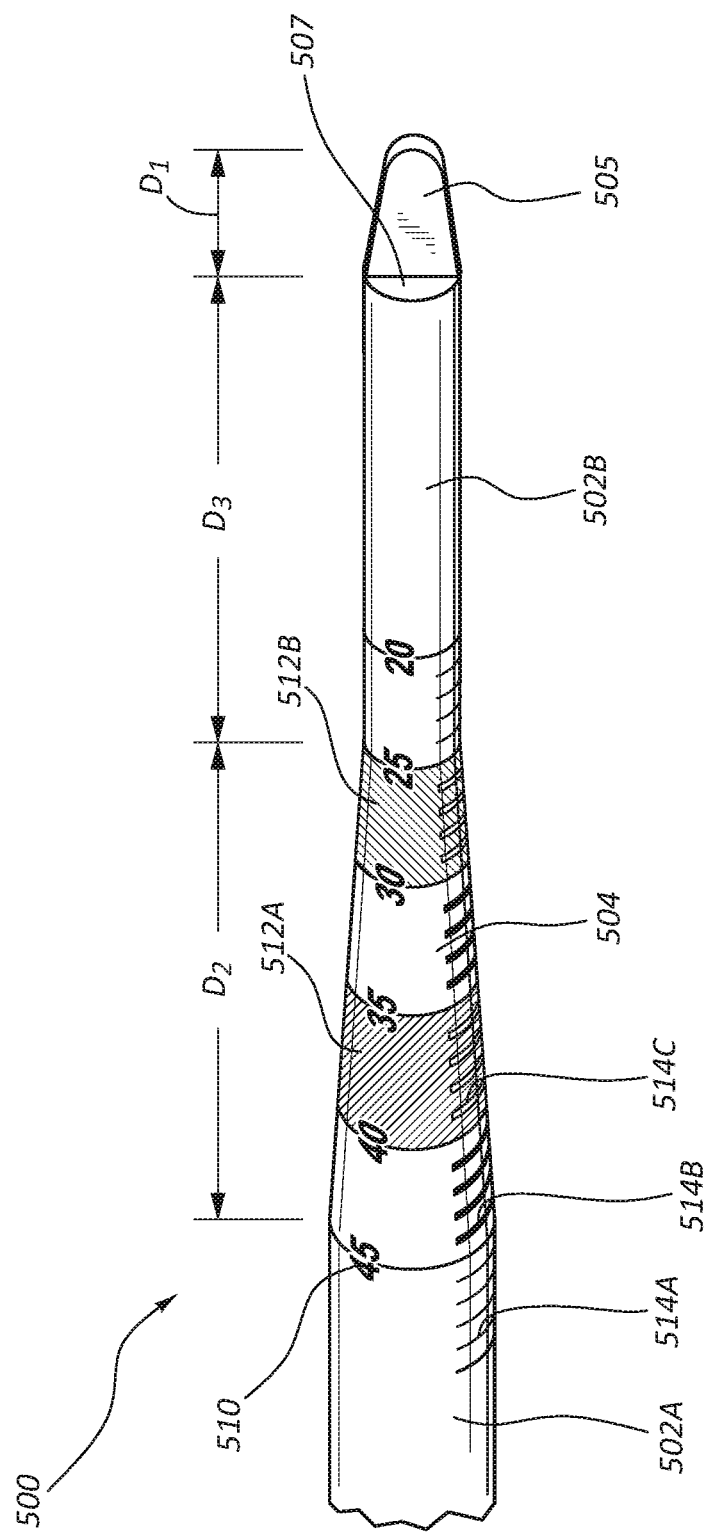
FIG. 5 depicts a vertebral probe according to other embodiments.

FIG. 5 depicts a vertebral probe 500 according to other embodiments. Probe 500 differs from probe 100 in several respects, any one or more of which may be applied to probe 100, or vice versa, in a piecemeal fashion as desired. First, probe 500 comprises two non-tapering portions, namely, a first or proximal non-tapering portion 502A and a second or distal non-tapering portion 502B. A tapering portion 504 is positioned in between non-tapering portions 502A and 502B.

Non-tapering portion 502B is configured to extend through a vertebral body during a probing procedure. Providing one or more such non-tapering portions may be useful to allow for easier penetration/excavation during this procedure, but preferably only for a precise, predetermined length that may be dictated by and/or correspond with the anatomy of the vertebral body being probed.

The tamping or other advancement of probe 500 may then be slowed by providing an adjacent tapering portion 504, which may add to the force required to advance the probe 500 further. The degree of force added may be proportional to the degree of tapering and may vary as desired depending upon other features of the probe, the structure of the vertebrae, and/or surrounding patient anatomy.

As mentioned above, the lengths of various sections of probe 500 may also vary in accordance with patient anatomy. For example, in some embodiments, non-tapering section 502B may comprise a distance D3 of between about 12 mm and about 20 mm for a small probe (with a more preferred distance being about 16 mm), between about 18 mm and about 25 mm for a medium probe (with a more preferred distance being about 21 mm), and between about 23 mm and about 30 mm for a large probe (with a more preferred distance being about 26 mm). Tapering section 504 may comprise a distance D2, which may be any desired length but preferably sufficiently long such that when probe 500 is fully positioned through a vertebral body with the tip protruding through the distal cortical wall, tapering section 504 is long enough to extend through the proximal cortical wall opening to provide resistance to advancement of the probe 500 during and/or prior to breach of the distal cortical wall.

Some embodiments may provide for a series of probes for use in connection with different patients and/or different vertebral bodies. However, in preferred embodiments and implementations, the "working section" of the probe (in other words, the portion of the probe that will enter the vertebrae), may be specifically tailored to the typical width of a vertebrae and therefore may have various distances that are proportional to one another. For example, in some embodiments, the distance D3 may be between about five and about seven times the length of D1. In this manner, the tapering section, which may act to inhibit advancement of the probe within a vertebral body, may begin at or near the point at which the tip makes contact with the inner surface of the distal cortical wall, which may provide enhanced safety and provide a surgeon with a tactile feel that is associated with this portion of the advancement. Similarly, in some embodiments, D1 may be between about 10 and about 25% of the length of D3.

As mentioned above in connection with probe 100, probe 500 further comprises a tip 505 defined in part by shelf 507. Again, tip 505 is preferably configured to allow for penetration through a cortical wall or other high-density bone portion and substantially increase the amount of force required to advance probe 500 further by providing a shelf for contacting this high-density wall. Thus, a surgeon will preferably be able to feel when shelf 507 has contacted both the proximal and distal cortical walls to assist in precise and safe placement of the probe and the subsequent bone screw/anchor. As also previously mentioned, distance D1 of tip 505 may be between about 2 and about 3 mm for a thoracic probe and may be between about 3 and about 5 mm for a lumbar probe. Thus, more generally speaking, in certain preferred embodiments, distance D1 may be between about 2 and about 6 mm. In some such embodiments, distance D1 may be between about 3 and about 5 mm.

Probe 500 also comprises several other features not shown or described in connection with probe 100. For example, probe 500 comprises a series of markings configured to further facilitate ease of use, safety, and/or subsequent screw/anchor placement. More particularly, probe 500 comprises a series of alphanumerical markings 510 along with a series of more precise markings (dash lines in the depicted embodiment) that may allow a surgeon to take very precise measurements of the vertebral anatomy and/or receive a very precise indication of the current placement of the probe 500.

In some embodiments, a series of adjacent sections comprising distinct markings of one or more types may be provided. Thus, probe 500 comprises a first series of dash lines 514A comprising relatively thin lines, a second series of dash lines 514B adjacent to the first series 514A comprising relatively thicker lines, a third series of dash lines 514C comprising still different dash lines (of a different color), and so on. By varying the sections, a surgeon may be provided with a more general view, once the surgeon becomes familiar with the marking system, of the probe 500 placement without having to rely on the alphanumerical markings 510, which may be most useful following full advancement of the probe 500 to provide the surgeon with a very precise indication of the width of the vertebral body to allow for screw selection.

Other distinct patterns/sections may be provided, either in addition to or as an alternative to those mentioned above. For example, in the depicted embodiment, two or more adjacent sections may be colored, patterned, and/or otherwise marked distinctly. Thus, each of the sections in between adjacent alphanumerical markings 510 may be colored, patterned, and/or otherwise marked distinctly. As shown in the figure, section 512A may therefore comprise a first color and section 512B may comprise a second color distinct from the first color. Sections immediately adjacent to sections 512A and 512B may similarly be visibly distinct from their adjacent sections. Thus, these sections are depicted as uncolored in the embodiment of FIG. 5. These more general markings may allow a surgeon to easily and immediately receive a general indication of the extent to which the probe 500 has penetrated a vertebral body. For example, a green section may indicate that the probe is in a central location within the vertebral body, a yellow section may indicate that the distal cortical wall is approaching, and a red section may indicate danger, such as that the probe is near or beyond the distal cortical wall. In some contemplated embodiments, one or more of these marking features may therefore be provided without the novel probe tip 505 disclosed herein.

Of course, those of ordinary skill in the art will appreciate a variety of alternative configurations to allow a surgeon to visualize an approximate location of a vertebral probe within a vertebral body without requiring precise numerical measurements and/or tick marks. Thus, the adjacent sections 512 with distinct markings spanning multiple more precise markings and the distinct patterns of dash lines 514 between adjacent sections are examples of means for coarsely visualizing a current location of a vertebral probe within a vertebral body. As mentioned above, the finer measurements provided by dash lines 514 may then be used, for example, to provide a precise measurement of the span of a vertebral body, which may be useful for bone screw selection.

In preferred embodiments, the markings on the probe may be visible from every side and/or angle of the probe. Thus, for example, duplicate markings may be positioned on the opposite side, or more than two sets of such markings may be provided. Similarly, in some embodiments, some or all of the markings may be staggered so that each marking is positioned slightly above or below the adjacent markings such that the markings gradually rotate about the probe.

FIG. 6 is an axial, front elevation view of a tip 605 of a vertebral probe according to some embodiments. As shown in this figure, tip 605 comprises flattened upper and lower surfaces and these surfaces may extend smoothly on the sides into the body of the probe. Thus, this design provides upper and lower shelves 607A and 607B, respectively, which, as discussed above, facilitate positioning of a probe through proximal and/or distal cortical walls adjacent to tip and may provide for tactile feel of such probe position.

Figure 7:
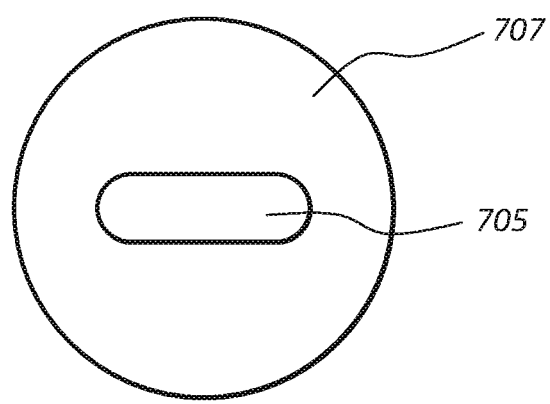
FIG. 7 is a side elevation view of another tip of a vertebral probe viewed along an elongated axis of the probe according to still other embodiments.

Alternatively, however, as shown in the axial, front elevation view of FIG. 7, the tip 705 may protrude from a central region of a single shelf 707. Still other embodiments are contemplated. For example, the sides of the probe tip may taper towards a rounded or pointed tip to form a tongue-like shape or may extend parallel to one another to form more of a table-top shape if desired.

However, it is contemplated that other non-symmetrical shapes may be used for vertebral probe tips, as desired. Thus, it may be preferred to have a probe body comprising a circular shape in cross-section with a tip that comprises a non-circular and/or non-symmetrical shape in cross-section, if not the flattened or "duckbill" shapes depicted in the figures.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims.

The invention claimed is:

1. A vertebral probe for use in spinal surgeries, comprising:
   a shaft having a circular cross section at least in part; and
   a tip having a length less than a length of the shaft, the tip being positioned at a distal end of the shaft adjacent to a portion of the shaft having a circular cross section and configured to penetrate a vertebral body to facilitate subsequent placement of a bone anchor providing bicortical purchase within the vertebral body, wherein the tip comprises a non-circular shape in cross-section at least in part, wherein the tip is defined, at least in part, by opposing flat surfaces extending from the shaft, wherein the vertebral probe further comprises two opposing shelves extending at an angle relative to each of the two opposing flat surfaces of the tip from a base of the tip, and wherein the portion of the shaft having the circular cross section extends proximally along the shaft from the base of the tip smoothly such that the shaft is configured to be non-rotatably advanced through bone of the vertebral body.

2. The vertebral probe of claim 1, wherein the shaft comprises a tapering portion and a non-tapering portion, and wherein the tapering portion tapers from a smaller cross-sectional diameter to a larger cross-sectional diameter proximally from the base of the tip.

3. The vertebral probe of claim 2, wherein the non-tapering portion is positioned adjacent to the tip, and wherein the tapering portion is positioned adjacent and proximally of the non-tapering portion.

4. The vertebral probe of claim 3, wherein the shaft further comprises a second non-tapering portion, wherein the tapering portion is positioned in between the non-tapering portion and the second non-tapering portion.

5. The vertebral probe of claim 1, wherein the vertebral probe is configured to allow for penetration of the tip through a cortical wall of a vertebral body with a first force and further configured to inhibit further advancement of the vertebral probe by requiring a second force substantially greater than the first force to achieve further advancement of the vertebral probe within the vertebral body, and wherein the tip comprises a blunt tip at the distalmost point of the tip.

6. The vertebral probe of claim 1, wherein the shaft comprises a plurality of markings configured to allow a user to identify a current position of the vertebral probe within a vertebral body.

7. The vertebral probe of claim 6, wherein the plurality of markings comprises a plurality of marking sections, wherein each marking section is visually distinguishable from an adjacent marking section other than with distinct alphanumeric characters about an entire circumference of the shaft such that the plurality of marking sections is configured to provide a user with an indication of an extent to which the vertebral probe has penetrated a vertebral body without use of alphanumeric characters from every side of the shaft, and wherein the plurality of markings further comprises alphanumeric characters that are positioned about an entire circumference of the shaft so as to be visible from every side of the shaft.

8. The vertebral probe of claim 1, wherein each of the two opposing shelves is at least substantially flat.

9. The vertebral probe of claim 1, wherein the two opposing shelves extend evenly about a base of the tip.

10. The vertebral probe of claim 1, wherein the tip has a length of between about 2 mm and about 6 mm.

11. The vertebral probe of claim 1, wherein the shaft comprises a circular cross-section along an entire length of the shaft, and wherein the shaft comprises a smooth outer surface along the entire length of the shaft.

12. A vertebral probe, comprising:
   a shaft comprising at least one tapering portion and at least one non-tapering portion, wherein the at least one tapering portion tapers from a smaller cross-sectional area to a larger cross-sectional area in a distal to proximal direction; and
   a tip positioned at a distal end of the shaft and configured to penetrate a vertebral body to facilitate subsequent placement of a bone anchor providing bicortical purchase within the vertebral body, wherein the tip is set apart from the shaft at a flattened shelf defining an engaging surface for evenly increasing an insertion force of the vertebral probe during non-rotational advancement through a vertebral body, wherein the shaft extends directly from and is positioned immediately adjacent to the flattened shelf, and wherein the shaft is configured to be non-rotatably advanced through bone of the vertebral body.

13. The vertebral probe of claim 12, wherein the tip comprises a non-circular shape in cross section.

14. The vertebral probe of claim 12, wherein the shelf extends about an entire periphery of the tip.

15. The vertebral probe of claim 12, further comprising a second shelf defining a second engaging surface for increasing an insertion force of the vertebral probe during advancement through a vertebral body.

16. The vertebral probe of claim 12, wherein the tip is defined, at least in part, by opposing flat surfaces extending from the shaft.

17. The vertebral probe of claim 16, wherein the tip is further defined by opposing tapered edges extending to a rounded and blunt tip at the distal-most end of the tip.

18. The vertebral probe of claim 12, wherein the flattened shelf extends evenly about an entire periphery of the tip.

19. The vertebral probe of claim 12, wherein the tip has a length of between 2 mm and 6 mm.

20. The vertebral probe of claim 12, wherein the shaft comprises a circular cross-section along an entire length of the shaft.

\* \* \* \* \*